United States Patent [19]

Lambert, Jr. et al.

[11] Patent Number: 4,510,326

[45] Date of Patent: Apr. 9, 1985

[54] PROCESS FOR THE PREPARATION OF FORMYLALKANOLAMINES

[75] Inventors: Clifford L. Lambert, Jr.; Roger G. Duranleau, both of Georgetown, Tex.

[73] Assignee: Texaco Inc., White Plains, N.Y.

[21] Appl. No.: 514,712

[22] Filed: Jul. 18, 1983

[51] Int. Cl.³ ............................................. C07C 102/00
[52] U.S. Cl. ...................................................... 564/132
[58] Field of Search .......................................... 564/132

[56] References Cited

U.S. PATENT DOCUMENTS

| | | | |
|---|---|---|---|
| 2,677,706 | 5/1954 | Giachino | 564/132 |
| 3,028,417 | 4/1962 | Eisenmann | 564/132 X |
| 4,098,820 | 7/1978 | Couteau et al. | 564/132 |
| 4,101,577 | 7/1978 | Smathers | 564/132 |

*Primary Examiner*—Paul F. Shaver

*Attorney, Agent, or Firm*—Robert A. Kulason; James J. O'Loughlin; Cynthia L. Kendrick

[57] ABSTRACT

A process for the preparation of a formylalkanolamine which comprises reacting carbon monoxide with an alkanolamine at a temperature ranging from about 60° to 300° C. and at a pressure ranging from about 100 to 10,000 psig, said alkanolamine being represented by the formula:

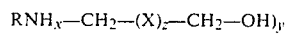

$$RNH_x-CH_2-(X)_z-CH_2-OH)_y$$

in which x is 0 or 1, R is hydrogen, a methyl or an aminoethyl radical with the proviso that R is hydrogen when x is 0, y is 1 or 2 and the sum of x and y is 2, X is a divalent radical from the group consisting of —CH$_2$— and —CHOH—, and z is 0 or 1.

9 Claims, No Drawings

PROCESS FOR THE PREPARATION OF FORMYLALKANOLAMINES

BACKGROUND OF THE INVENTION

1. Field of the Invention

The carbonylation of ammonia or amines to prepare formamides is known. In the currently employed process to prepare formamides, ammonia and carbon monoxide are reacted at temperatures of 80° to 100° C. and at pressures of 100 to 300 atmospheres in the presence of methanolic sodium methoxide. Similarly, to prepare dimethyl formamides, dimethylamine and carbon monoxide are reacted at temperatures of 110° to 150° C. and at pressures of 15 to 25 bar in the presence of sodium methylate or metal carbonyls. However, efforts to react ammonia and carbon monoxide directly under conditions of high pressure and high temperature were not successful: severe technical problems were encountered and only low yields of formamide were obtained.

The present process is directed to a process for preparing formylalkanolamines which are a particular class of formamides, namely, hydroxyalkylformamides. Attempts to employ conventional methanolic sodium methoxide catalyst technology to carbonylate alkanolamines have proven to be unsatisfactory. With an alkanolamine as the reactant, the equilibrium point of the carbonylation reaction process is shifted away from product formation, making it difficult or impossible to get a useful yield of formylalkanolamine.

It is an object of this invention to provide a novel process for the preparation of a specific class of formylalkanolamines.

It is another object of this invention to provide a method for extracting carbon monoxide from an impure gas stream containing the same.

2. Disclosure Statement

Kirk-Othmer, *The Encyclopedia of Chemical Technology* (Third Edition, Vol. 11) at pages 259 and 264 to 265 discloses carbonylation reactions with ammonia and amines wherein ammonia or an amine are reacted with carbon monoxide in the presence of a solvent containing a basic catalyst, for example, sodium methoxide in methanol, at temperatures ranging from 80° to 200° C. and at pressures ranging from 400 to 1500 psig to produce the corresponding formamide or dimethylformamide.

An article in Chemical Abstracts (47:9724-5) discloses the absorption of carbon monoxide by a solution containing cuprous monoethanolamine complex.

SUMMARY OF THE INVENTION

This invention relates to a process for the preparation of a formylalkanolamine which comprises reacting carbon monoxide with a prescribed class of alkanolamines, with the reaction being conducted at temperatures ranging from about 60° to 300° C. and at pressures ranging from about 100 to 10,000 psig. The alkanolamine which can be employed are represented by the formula:

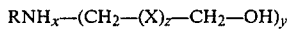

in which x is 0 or 1, R is hydrogen, a methyl, or an aminoethyl radical with the proviso that R is hydrogen when x is 0, y is 1 or 2 and the sum of x and y is 2, X is a divalent radical from the group consisting of —$CH_2$— and —CHOH—, and z is 0 or 1.

DETAILED DESCRIPTION OF THE INVENTION

The invention relates to a process for the preparation of formylalkanolamines which comprises reacting carbon monoxide with an alkanolamine of the following formula:

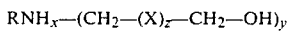

in which x is 0 or 1, R is hydrogen, a methyl, or an aminoethyl radical with the proviso that R is hydrogen when x is 0, y is 1 or 2 and the sum of x and y is 2, X is a divalent radical from the group consisting of —$CH_2$— and —CHOH—, and z is 0 or 1.

More specifically the alkanolamines which can be employed in the instant process include monoethanolamine, diethanolamine, 2-(2 aminoethylamino)-ethanol, 1-amino-3-propanol, 1-amino-2,3-propanediol, N-methylethanolamine, and 3-(2-aminoethyl)aminopropane-1,2 diol.

The reaction occurs at temperatures ranging from 60° to 300° C. and pressures ranging from 100 to 10,000 psig. The preferred temperature range is 100° to 250° C. and the preferred pressure range is 200 to 5000 psig, with the most preferred temperature range being 140° to 200° C. and the most preferred pressure range being 400 to 2000 psig.

The carbon monoxide employed may be supplied in either pure form, that is, without any other gaseous components, or as a gas mixture. The reaction proceeds with the alkanolamine reacting only with the carbon monoxide and with no other gases, even if these other gases are present at the time of reaction.

The instant reaction process is particularly useful in regulating the amount of carbon monoxide present in systems where such control is important. One such system where the present process can be employed is in synthesis gas processing; another is in blast furnace gas treatment. A feature that makes this process advantageous for effecting carbon monoxide separation and purification is that the gas streams do not have to be pretreated. Moreover, in synthesis gas systems, by controlling the amount of alkanolamine reactant present, the instant method can be employed to change the carbon monoxide/hydrogen ratio and, as the process is reversible, the carbon monoxide which is taken out of the gas stream can be regenerated in a desired location.

The Examples below demonstrate that with the exception of N-methylethanolamine, the alkanolamines reacted with carbon monoxide in rapid fashion and produced an end product that was nearly all comprised of the desired formylalkanolamine.

EXAMPLE 1

Production of Formylethanolamine 183 grams (about 3.0 moles) of monoethanolamine was charged to an autoclave which was then pressurized with carbon monoxide to 900 psig and heated to 150° C. The pressure was then increased to 1600 psig and as the carbon monoxide was consumed the reactor was periodically repressurized with carbon monoxide. After 4 hours, the autoclave was cooled and contents of the system collected and analyzed. By NMR analysis the 261 grams of product was shown to be essentially pure formylethanolamine. This was further confirmed by hydroxyl number (656 mg KOH/g) and total amine analysis (0.008 meq/g).

EXAMPLE 2

Production and Purification of Formyldiethanolamine 420 grams (about 4.0 moles) of diethanolamine was charged to an autoclave which was evacuated at about 20° C. and then pressurized with carbon monoxide to 900 psig. The autoclave was then heated to 150° C., at which point carbon monoxide was charged to the system over a 5 hour period until a pressure of 1665 psig was reached. The autoclave was then cooled, vented, and the product removed. Analysis of the product indicated that essentially pure formyldiethanolamine was formed.

A crude solution of the product (248 grams) was passed over the acid form of AMBERLITE® I.R. 200 (430 grams of resin). The product after filtering to remove traces of resin was found to be essentially pure formyldiethanolamine as shown by hydroxyl number (811 mg KOH/g), total amine analysis (0.004 meq/g) and NMR analysis.

EXAMPLE 3

Production of Formyl-2-(2 aminoethylamino)-ethanol 208 grams (about 2 moles) of 2-(2 aminoethylamino)-ethanol was charged to an autoclave and treated in the same manner as in Example 1. After 16 hours, 258 grams of product were produced. NMR analysis indicated complete consumption of the starting materials and, as a result of the partial formylation which takes place at each amine group, the formation of a mixture of two formamides. Based on theoretical calculations, a product yield of 97.7% was achieved.

EXAMPLE 4

Production of Formyl-1-amino-3-propanol 75 grams (about 1 mole) of 1-amino-3-propanol was charged to an autoclave and reacted in the same manner as in Example 1. The product (82 grams) was shown by NMR analysis to be free of starting material and to be essentially pure formyl-1-amino-3-propanol.

EXAMPLE 5

Production of Formyl-1-amino-2,3-propanediol 100.0 g (about 1.03 mole when 93.93% pure) of 1-amino-2,3-propanol and carbon monoxide were reacted in a "magne-dash" reactor at 155° C. and at 880 psig. By repressurizing the reactor with carbon monoxide whenever the pressure fell to 600 psig, the pressure in the reactor was maintained at the starting pressure of 880 psig. This process was repeated until no further consumption of carbon monoxide was observed. The vessel was then opened, and the contents removed. The products and starting material were analyzed by NMR and wet techniques. The results of the test show that the product (108 grams) was nearly all (greater than 98%) N-formyl-1-amino-2,3-propanediol. Based on theoretical calculations, a product yield of 87.9% was achieved.

EXAMPLE 6

Production of Formyl-N Methylethanolamine 45.0 grams (about 0.61 moles) of N-methylethanolamine and carbon monoxide were reacted at 155° C. for 14 hours in a rocking autoclave. As the carbon monoxide gas was gradually consumed, the system pressure decreased to 1390 psig, and the autoclave was repressurized with carbon monoxide to 1500 psig. After 14 hours, it was observed that there was no further consumption of carbon monoxide. The product (56.0 grams) was then removed and analyzed by NMR techniques which showed the product to be a mixture of 28% starting material and 72% formyl-N-methylethanolamine.

EXAMPLE 7

Production of Formyl-3-(2-aminoethyl)aminopropane-1,2-diol 20.0 grams (0.149 moles) of 3-(2-aminoethyl)aminopropane-1,2-diol was placed in a rocking autoclave that was flushed with carbon monoxide at a system pressure of under 100 psig and then sealed. Subsequently, the alkanolamine was reacted with carbon monoxide at a temperature of 155° C. and at a carbon monoxide pressure of 1500 psig with the autoclave being repressurized with carbon monoxide whenever the pressure dropped to 1400 psig. After 5 hours, the reaction was stopped and the 20.2 grams of liquid product were analyzed by proton NMR technique which determined, as evidenced by the indicia of formamide bonds in the 8.0 to 8.4 ppm of the spectra, that about 85% of the product mixture comprised formamide compounds, including, among others, formyl-3-(2-aminoethyl)aminopropane-1,2-diol.

EXAMPLE 8

Employing the Instant Reaction with Other Amines and Alkanolamines

In a rocking autoclave, in like manner to the previously described experiments, various other amines and alkanolamines were subjected to a temperature of 155° C. and a carbon monoxide pressure of 1290 psig. Specifically, the amines and alkanolamines employed included diglycolamine; 1-amino-2-propanol; morpholine and 1-butanol; morpholine and diethyleneglycol; various amines, including 3-methoxypropylamine, Jeffamine ®D-230, and ethylenediamine; various alkanolamines, including hydroxyethylpiperazine, triethanolamine, 0-aminophenol, N-2-hydroxyethylaniline, L-2-amino-1-butanol, 4-aminobutanol-1, 5-amino-1-ketanol, and N-ethylethanolamine; and glycine.

During the reaction period there was no appreciable uptake of carbon monoxide gas. NMR analysis of autoclave contents indicated that none of the above-named amines or alkanolamines had reacted with the carbon monoxide, with the exception of diglycolamine where only a 10% yield of the desired formyldiglycolamine product was obtained.

EXAMPLE 9

Preparation of Formylethanolamine Employing Synthesis Gas

Synthesis gas comprising carbon monoxide and hydrogen in a 1:1 ratio and 237 gms (3.88 moles) of monoethanolamine were introduced into an autoclave which was then pressurized to 2440 psig and the contents thereof heated to 150°–155° C. When over the course of the reaction the total pressure dropped to 1790 psig, the reactor was repressurized by the addition of carbon monoxide to 2000 psig. After 7 hours, the system was cooled, vented, and the liquid product removed. There was recovered 287 grams of product (i.e., a 46% conversion rate) which NMR analysis showed to be formylethanolamine.

EXAMPLE 10

Preparation of Formyldiethanolamine Employing Synthesis Gas

Synthesis gas comprising carbon monoxide and hydrogen in a 1:1 ratio and diethanolamine were introduced into an autoclave. At a temperature of 147° to 150° C. and an initial starting pressure of 2700 psig the contents of the autoclave were reacted. During the course of the reaction, the pressure fell to 2300 psig, and the reactor was by the addition of carbon monoxide repressurized to the initial pressure level of 2700 psig. After 9 hours the autoclave was cooled, vented and emptied. There was recovered 30 grams of product, which NMR analysis found to be formyldiethanolamine.

When heated at atmospheric or sub-atmospheric pressure, the formylalkanolamine undergoes a decarbonylation reaction in which carbon monoxide is released. By supplying pure carbon monoxide, this decarbonylation reaction would be especially useful in, for example, synthesis gas processing operations where the amount of carbon monoxide present in a gaseous mixture must be carefully controlled.

This invention demonstrates that formylalkanolamines can be prepared by reacting carbon monoxide and certain prescribed alkanolamines under specified pressure and temperature conditions. This was surprising since many alkanolamines do not react with carbon monoxide to form a formylalkanolamine.

What is claimed:

1. A process for the preparation of a formylalkanolamine which comprises reacting carbon monoxide with an alkanolamine at a temperature ranging from about 60° to 300° C. and a pressure ranging from about 100 to 10,000 psig, said alkanolamine being represented by the formula:

$$RNH_x-(CH_2-(X)_z-CH_2-OH)_y$$

in which x is 0 or 1, R is hydrogen, a methyl, or an aminoethyl radical with the proviso that R is hydrogen when x is 0, y is 1 or 2 and the sum of x and y is 2, X is a divalent radical from the group consisting of $-CH_2-$ and $-CHOH-$, and z is 0 or 1.

2. A process according to claim 1 wherein the alkanolamine employed is monoethanolamine.

3. A process according to claim 1 wherein the alkanolamine employed is diethanolamine.

4. A process according to claim 1 wherein the alkanolamine employed is 2-(2 aminoethylamino)-ethanol.

5. A process according to claim 1 wherein the alkanolamine employed is 1-amino-3 propanol.

6. A process according to claim 1 wherein the alkanolamine employed is N-methylethanolamine.

7. A process according to claim 1 wherein the alkanolamine employed is 3-(2-aminoethyl)aminopropane-1,2 diol.

8. A process according to claim 1 wherein the temperature employed ranges from 100° to 250° C. and the pressure employed ranges from 200 to 5000 psig.

9. A process according to claim 1 wherein the temperature employed ranges from 140° to 200° C. and the pressure employed ranges from 400 to 2000 psig.

* * * * *